(12) United States Patent
Mango (10) Patent No.: US 7,435,597 B2
(45) Date of Patent: Oct. 14, 2008

(54) ASSAYS FOR ZERO-VALENT TRANSITION METALS IN SEDIMENTARY ROCKS USING CARBON MONOXIDE WITH APPLICATION TO OIL AND GAS EXPLORATION

(75) Inventor: Frank D. Mango, Houston, TX (US)

(73) Assignee: Petroleum Habitats, L.L.C., Houston, TX (US)

( * ) Notice: Subject to any disclaimer, the term of this patent is extended or adjusted under 35 U.S.C. 154(b) by 933 days.

(21) Appl. No.: 10/830,266

(22) Filed: Apr. 21, 2004

(65) Prior Publication Data

US 2005/0239206 A1 Oct. 27, 2005

(51) Int. Cl.
G01N 33/20 (2006.01)
G01N 33/24 (2006.01)

(52) U.S. Cl. .......................... 436/31; 73/152.01; 436/25; 436/26; 436/29; 436/73; 436/84; 436/161; 436/181; 436/182

(58) Field of Classification Search .............. 73/152.01; 436/25–26, 29, 31, 73, 84, 161, 181–182
See application file for complete search history.

(56) References Cited

U.S. PATENT DOCUMENTS

| | | | | |
|---|---|---|---|---|
| 3,343,917 A | * | 9/1967 | Friedman | 436/31 |
| 3,428,431 A | * | 2/1969 | Billings | 436/29 |
| 3,934,455 A | * | 1/1976 | Harrisberger | 436/5 |
| 4,108,552 A | * | 8/1978 | Austin et al. | 356/315 |
| 4,205,956 A | * | 6/1980 | Stedman | 436/84 |
| 4,426,452 A | * | 1/1984 | Lasoski | 436/76 |
| 4,587,847 A | * | 5/1986 | Malmqvist et al. | 73/28.01 |
| 5,174,966 A | * | 12/1992 | Durand et al. | 422/102 |

OTHER PUBLICATIONS

Lee, D. S., Analytical Chemistry 1982, 54, 1182-1184.*
Drews, W. et al, Fresenius' Zeitschrift fuer Analytische Chemie 1989, 332, 862-865.*
Schaefer, W., Fresenius' Zeitschrift fuer Analytische Chemie 1989, 335, 785-790.*
Mihaylov, M. et al, Catalysis Letters 2001, 76, 59-63.*
Mango, et al., "The catalytic decomposition of petroleum into natural gas," Geochimica et cosmochimica Acta, 61:5347-5350 (Aug. 1997).
Mango, "The origin of light hydrocarbons," Geochimica et cosmochimica Acta, 64:1265-1277 (Sep. 1999).
Mango, "The light hydrocarbons in petroleum: a critical review," Org. Geochem., vol. 26, No. 7/8, pp. 417-440 (May 1997).
Mango, "Methane concentrations in natural gas: the genetic implications," Org. Geochem., 32:1283-1287 (Jul. 2001).

(Continued)

Primary Examiner—Arlen Soderquist
(74) Attorney, Agent, or Firm—Winstead PC (57) ABSTRACT

The present invention is directed to novel assays for zero-valent transition metals. The novel assays of the present invention are generally methods or processes for quantitatively and/or qualitatively evaluating the presence of zero-valent transition metals on and/or within samples. Such assays generally involve a digestion process whereby the sample is exposed to carbon monoxide. Transition metals, if present in or on the sample and if contacted by the carbon monoxide, are extracted by the carbon monoxide as metal carbonyl species, the presence of which confirms the presence of transition metals. Such novel assays have enormous predictive power in oil and gas exploration.

34 Claims, 3 Drawing Sheets

OTHER PUBLICATIONS

Air Products & Chemicals, Inc., et al., Excerpt of Topical Report entitled "Alternative Fuels Field Test Unit Support to Kingsport LPMEOH™ Demonstration Unit," (Dec. 1997). p. 17 only.

Excerpt from website http://www.angelfire.com/trek/galactic mining/carbonyl.htm, "Near Earth Asteroid Utilization and Carbonyl Metallurgical Processes," (Apr. 2002) 2 pages.

Hunt, Petroleum Geochemistry and Geology, 2nd ed., W. H. Freeman, New York., Chapter 7 (1996), pp. 185-223 and 236-237.

Paine, et al., "Geology of Natural Gas in South Louisiana," American Association of Petroleum Geologists, Memoir 9, vol. 1, Natural Gases of North America, Beebe, B. W., Editor, 376-581 (Nov. 1966).

Price, "Thermal stability of hydrocarbons in nature: Limits, evidence, characteristics, and possible controls," Geochimica et Cosmochimica Acta, 57:3261-3280 (Mar. 1993).

Littke, et al., "Gas Generation and Accumulation in the West Siberian Basin," AAPG Bulletin, 83:1642-1665 (Oct. 1999).

Domine, et al., "Towards a new method of geochemical kinetic modelling: implications for the stability of crude oils," Organic Geochemistry, 28:597-612 (Mar. 1998).

Domine, et al., "Up to what temperature is petroleum stable? New insights from 5200 free radical reaction model," Organic Geochemistry, 33:1487-1499 (2002).

Mallinson, et al., "Detailed Chemical Kinetics Study of the Role of Pressure in Butane Pyrolysis," Industrial & Engineering Chemistry Research, 31:37-45 (Jun. 1991).

Burnham, et al., "Unraveling the Kinetics of Petroleum Destruction by Using 1,2_13C Isotopically Labeled Dopants," Energy & Fuels, 9:190-191 (May 1994).

Jackson, et al., "Temperature and pressure dependence of n-hexadecane cracking," Organic Geochemistry, 23:941-953 (Aug. 1995).

Mango, "Transition metal catalysis in the generation of petroleum and natural gas," Geochimica et Cosmochimica Acta., 56:553-555 (Dec. 1991).

Mango, et al., "The carbon isotopic composition of catalytic gas: A comparative analysis with natural gas," Geochimica et Cosmochimica Acta, 63:1097-1106 (Jan. 1999).

Boggs, Jr., "Principles of Sedimentology and Stratigraphy," Prentice-Hall, Inc., 2nd ed., pp. 165 & 195 (1995).

Medina, et al., "Low temperature iron- and nickel-catalyzed reactions leading to coalbed gas formation," Geochimica et Cosmochimica Acta, 64:643-649 (Feb. 2000).

Galbreath, et al., "Chemical Speciation of Nickel in Residual Oil Ash," Energy & Fuels, 12:818-822 (Jun. 1998).

Seewald, "Organic-inorganic interactions in petroleum-producing sedimentary basins," Nature, 426:327-333 (Nov. 2003).

Mann, et al., "Organic Facies Variations, Source Rock Potential, and Sea Level Changes in Cretaceous Black Shales of the Quebrada Ocal, Upper Magdalena Valley, Colombia," American Association of Petroleum Geologests Bulletin, 81:556-576 (Apr. 1997).

Cruickshank, et al., "Mineral Deposits at the Shelfbreak," SEPM Special Publication No. 33, (Jun. 1983) pp. 429-431.

* cited by examiner

ASSAYS FOR ZERO-VALENT TRANSITION METALS IN SEDIMENTARY ROCKS USING CARBON MONOXIDE WITH APPLICATION TO OIL AND GAS EXPLORATION

TECHNICAL FIELD

The present invention relates in general to assays for zero-valent transition metals, and specifically to assays for evaluating the presence and concentration of zero-valent transition metals in sedimentary rocks for oil and gas exploration.

BACKGROUND INFORMATION

Oil progresses to natural gas in deep sedimentary basins. This process, hereafter referred to as "oil-to-gas," is believed to be the major source of natural gas in the earth (Hunt, *Petroleum Geochemistry and Geology*, 2$^{nd}$ ed., W. H. Freeman, New York., Chapter 7, 1996). Knowing when and how this process occurs is the key to predicting the distribution of oil and gas with depth. The conventional view is that oil thermally cracks to gas (thermal gas) at temperatures between 150° C. and 200° C., the observed temperature range where most oil-to-gas occurs. Various kinetic models (thermal models) based on this theory have had only marginal success, however, and there are glaring contradictions. Oil, for example, is found in deep reservoirs (>20,000 ft) at temperatures where it should not exist (Paine et al., "Geology of natural gas in South Louisiana," American Association of Petroleum Geologists, Memoir 9, Volume 1, Natural Gases of North America, Beebe, B. W., Editor, 376-581, 1968; Price, "Thermal stability of hydrocarbons in nature: Limits, evidence, characteristics, and possible controls," *Geochimica et Cosmochimica Acta*, 57:3261-3280, 1993), and giant deposits of so-called thermal gas exist in shallow reservoirs that cannot be explained by the thermal model without invoking long-range migration from deeper horizons (Littke et al., "Gas generation and accumulation in the West Siberian basin," *AAPG Bull.*, 83:1642-1665, 1999).

There is now mounting scientific evidence against the thermal models. From a series of laboratory experiments under realistic conditions (Domine et al., "Towards a new method of geochemical kinetic modelling: implications for the stability of crude oils," *Organic Geochemistry*, 28:597-612, 1998; Domine et al., "Up to what temperature is petroleum stable? New insights from 5200 free radical reaction model," *Organic Geochemistry*, 33:1487-1499, 2002), evidence now suggests that oil should not crack to gas over geologic time at temperatures between 150° C. and 200° C., the range within which most so-called thermal gas is formed, a conclusion supported by numerous other studies (Mallinson et al., "Detailed chemical kinetics study of the role of pressure in butane pyrolysis," *Industrial & Engineering Chemistry, Research*, 31:37-45, 1992; Burnham et al., "Unraveling the kinetics of petroleum destruction by using 1,2$^{13}$C isotopically labeled dopants," *Energy & Fuels*, 9:190-191, 1995; Jackson et al., "Temperature and pressure dependence of n-hexadecane cracking," *Organic Geochemistry*, 23:941-953, 1995). Moreover, the gas produced in oil cracking is severely depleted in methane and does not resemble natural gas as it is distributed in the earth (Mango, "The origin of light hydrocarbons," *Geochimica et Cosmochimica Acta*, 64:1265-1277, 2001).

Catalysis by transition metals is an alternative explanation for oil-to-gas (Mango, "Transition metal catalysis in the generation of petroleum and natural gas," *Geochimica et Cosmochimica Acta*. 56:553-555, 1992), and there is experimental evidence supporting it. Crude oils are converted to gas over zero-valent transition metals (ZVTM) (Ni, Co, and Fe) under moderate laboratory conditions (150-200° C.) and the products are identical to natural gas in molecular and isotopic composition (Mango and Hightower, "The catalytic decomposition of petroleum into natural gas," *Geochimica et Cosmochimica Acta*, 61:5347-5350, 1997; Mango and Elrod, "The carbon isotopic composition of catalytic gas: A comparative analysis with natural gas," *Geochimica et Cosmochimica Acta*, 63:1097-1106, 1998; Mango, "The origin of light hydrocarbons," *Geochimica et Cosmochimica Acta*, 64:1265-1277, 2000).

The above-described experiments are highly relevant to the generation of natural gas in sedimentary basins. Transition metals are common in sedimentary rocks (Boggs, S., Jr., *Principles of Sedimentology and Stratigraphy*, 2$^{nd}$ ed., Prentice-Hall, Inc., NJ, pages 165 & 195, 1995), and could become catalytically active (i.e., reduced to zero-valencies) given the reducing conditions of petroleum habitats (Mango, "The light hydrocarbons in petroleum: a critical review," *Organic Geochemistry*, 26:417-440, 1997; Mango, "The origin of light hydrocarbons," *Geochimica et Cosmochimica Acta*, 64:1265-1277, 2000; Medina et al., "Low temperature iron- and nickel-catalyzed reactions leading to coalbed gas formation," *Geochimica et Cosmochimica Acta*, 64:643-649, 2000; Seewald, "Organic-inorganic interactions in petroleum-producing sedimentary basins," *Nature*, 426:327-333, 2003). All requisites are in place: transition metal oxides in sufficient amounts to promote the reaction and enough hydrogen to activate them to zero-valencies and drive the reaction at subsurface temperatures (Mango, "The origin of light hydrocarbons," *Geochimica et Cosmochimica Acta*, 64:1265-1277, 2000).

Catalysis may be the source of the huge gas deposits in the Gulf Coast geosyncline of south Louisiana (Paine et al., "Geology of natural gas in South Louisiana," American Association of Petroleum Geologists, Memoir 9, Volume 1, Natural Gases of North America, Beebe, B. W., Editor, 376-581, 1968). Oil is generally found at depths above 10,000 feet and gas is generally found below such depths, consistent with the thermal model. However, gas probabilities are also a strong function of reservoir composition: low in pure sandstone and high in sandstones interbedded with outer-neritic shales that are often enriched in transition metals (Mann and Stein, "Organic facies variations, source rock potential, and sea level changes in Cretaceous black shales of the Quebrada Ocal, Upper Magdalena Valley, Colombia," *American Association of Petroleum Geologests Bulletin*, 81:556-576, 1997; Cruickshank and Rowland, "Mineral deposits at the shelf-break," SEPM Special Publication No. 33, 429-436, 1983).

Given high enough temperatures and hydrogen partial pressures at depth, transition metals in outer-neritic shales could attain zero-valencies. Thus activated, in-reservoir catalytic oil-to-gas would commence. In this instance, the important factor for predicting oil or gas in reservoir rocks is the presence of ZVTM in sufficient concentrations to promote catalytic oil-to-gas. A rock assay specific to ZVTM in outcrop rocks, cuttings, or core samples would thus be a powerful exploration tool for reservoirs that either preserve oil (no ZVTM) or convert it to gas (with ZVTM).

Applicant is unaware of any practical tests for trace amounts (i.e., ppm or less) of ZVTM in sedimentary rocks. Most rock methods use spectroscopic techniques, such as atomic absorption (AA) spectroscopy or inductively-coupled plasma atomic emission spectroscopy (ICP-AES), that do not differentiate between oxidation states. Nickel valency speciation has been achieved by X-ray absorption fine-structure spectroscopy using the National Synchrotron Light Source at Brookhaven National Laboratory (NY) and with anodic stripping voltammetry (Galbreath et al., "Chemical speciation of Nickel in residual oil ash," *Energy & Fuels*, 12:818-822, 1998), but the complexities of these methods preclude their use in routine rock analysis. Thus, a convenient assay for ZVTM would be highly-desirable, especially when used to detect and measure such species in sedimentary rock for the purpose of making predictions in oil and gas exploration.

SUMMARY OF THE INVENTION

The present invention is directed to novel assays for zero-valent transition metals (ZVTM). The novel assays of the present invention are generally methods or processes for quantitatively and/or qualitatively evaluating the presence of ZVTM and/or within samples. Furthermore, the application to oil and gas exploration provides for revolutionary advances in the predictability of oil and gas deposits based upon the levels of ZVTM present in the surrounding sedimentary rock.

In some embodiments, the present invention is a process comprising: exposing a sample that potentially comprises ZVTM to carbon monoxide in an exposure environment such that the carbon monoxide reacts with at least some of the ZVTM, if present, to form metal carbonyl species within the exposure environment subsequent to carbon monoxide exposure; and analyzing the exposure environment, subsequent to sample exposure, for metal carbonyl species, wherein such analyzing for metal carbonyl species yields information about the levels of ZVTM potentially present in said sample.

In some or other embodiments, the present invention is a process comprising: providing sedimentary rock sample potentially comprising a quantity of at least one zero-valent transition metal; exposing the sedimentary rock sample to carbon monoxide in an exposure environment under conditions effective for reacting at least some of the zero-valent transition metal potentially present with carbon monoxide to form metal carbonyl species; and analyzing the exposure environment, after a time sufficient to allow for at least some of the potentially-present ZVTM to react with the carbon monoxide, so as to establish the presence of such species within the sample In some of the above-described embodiments, the quantification of the metal carbonyl presence, in and/or on the sedimentary rocks, is used in making predictive determinations relevant to oil/gas exploration. Such predictive determinations are based upon the required presence of ZVTM for catalytic conversion of heavier hydrocarbons to natural gas.

In some embodiments, reaction of ZVTM with carbon monoxide ("CO digestion") is primarily a surface phenomenon. In such cases, the levels of ZVTM, relative to the surface area and/or surface area per unit mass of the sample, can be quantified by quantifying the metal carbonyl species in the exposure environment and the surface area and/or surface area per unit mass of the sample.

Depending on the embodiment and sample, one or more ZVTM may be digested and analyzed for the corresponding transition metal carbonyl. Analysis of the one or more transition metal carbonyl species can be carried out with a variety of existing analytical and/or separation techniques.

The methods and processes of the present invention offer tremendous advantages over existing methods of zero-valent transition metal detection in that they are relatively simple and easy to carry out. As such, they offer better accessibility, portability, and efficiency. Ultimately, because of their ease of operation, such processes have the potential to become standard protocol in oil/gas exploration.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION

The present invention is directed to novel assays for zero-valent transition metals (ZVTM). The novel assays of the present invention are generally methods or processes for quantitatively and/or qualitatively evaluating the presence of ZVTM on and/or within samples. Furthermore, the application to oil and gas exploration provides for revolutionary advances in the predictability of oil and gas deposits based upon the levels of ZVTM present in the surrounding sedimentary rock.

While most of the terms used herein will be recognizable to those of skill in the art, the following definitions are nevertheless put forth to aid in the understanding of the present invention. It should be understood, however, that when not explicitly defined, terms should be interpreted as adopting a meaning presently accepted by those of skill in the art.

"Sedimentary rock," as defined herein, refers generally to rock formed by the accumulation and cementation of mineral grains transported by wind, water, or ice to the site of deposition or chemically precipitated at the depositional site. A "sedimentary basin," as defined herein, is an accumulation of a large thickness of sediment, as in sedimentary rock. "Source rock," as defined herein, is sedimentary rock, usually shale or limestone, deposited together with the organic material which under pressure, heat, and time was transformed to liquid or gaseous hydrocarbons. "Outcrop rocks," as defined herein, generally refers to segments of bedrock exposed to the atmosphere.

A "gas habitat," as defined herein, refers to a "reservoir" within a sedimentary basin that contains greater than or equal to ($\geq$) some critical concentration X of ZVTM as determined by some appropriate assay such that it, a reservoir with X parts-per-million (ppm) ZVTM, will convert 90% of its contained oil to gas in some specified period of geologic time t, typically 10 million years (Ma) for basins where subsidence rates place reservoirs at temperature T ($\pm 10°$ C.) for 10 Ma. For basins with more or less rapid subsidence rates, time t is adjusted accordingly. A linear curve for each time period t showing critical ppm ZVTM versus reservoir temperature T can be constructed from the Arrhenius equation in Mango, "Transition metal catalysis in the generation of natural gas," *Organic Geochemistry*, 24:977-984, 1996, assuming Ni is equivalent to ZVTM. An "oil habitat," as defined herein, refers to a "reservoir" within a sedimentary basin that contains less than (<) X ppm ZVTM. Thus, there is a high probability of finding gas in a target reservoir designated a "gas habitat" and oil in a target reservoir designated an "oil habitat".

"Oil-to-gas," as defined herein, refers to geological processes in which crude oil (higher molecular weight hydrocarbons) converts into natural gas (lower molecular weight hydrocarbons). In the "thermal model," as defined herein, which is the generally accepted but imperfect model, oil-to-gas proceeds through thermal cracking and is thus a function of reservoir temperature and geologic time. Oil-to-gas in the "catalytic model," as defined herein, refers to a newer, but experimentally confirmed process, whereby oil is catalytically converted to gas with the aid of ZVTM. See Mango et al., "Role of transition-metal catalysis in the formation of natural gas," *Nature*, 368:536-538, 1994. The reservoir rock in the catalytic model is an active agent in oil-to-gas and a passive agent in the thermal model. Concentrations of ZVTM control oil-to-gas rates in the catalytic model and the kinetic parameters associated with thermal cracking control oil-to-gas rates in the thermal model. The two models have profoundly different predictive powers in oil and gas exploration.

An "active reservoir," as defined herein and in accordance with the oil-to-gas catalytic model, refers to a reservoir in which the surrounding sedimentary rock comprises≧critical concentrations of ZVTM as defined above. An "inactive reservoir," as defined herein and in accordance with the oil-to-gas catalytic model, refers to a reservoir<critical concentrations of ZVTM.

"Transition metal," as defined herein, refers to metals comprised of elements of the "d-block" of the Periodic Table. Specifically, these include elements 21-29 (scandium through copper), 39-47 (yttrium through silver), 57-79 (lanthanum through gold), and all known elements from 89 (actinium) on. Iron (Fe), cobalt (Co), and nickel (Ni) all have special relevance, however, due to their established catalytic activity. See Mango and Hightower, "The catalytic decomposition of petroleum into natural gas," *Geochimica et Cosmochimica Acta*, 61:5347-5350, 1997. "Zero-valent transition metal(s)," as used herein, are transition metals in their zero-oxidation (i.e., neutral) state.

"Metal carbonyl," as defined herein, refers to molecular metal compounds or complexes of the general formula $M(CO)_n$, where "M" is a zero-valent transition metal and carbon monoxide (CO) is a ligand. Such species are selectively formed by the reaction of CO with transition metals in their zero-valent state.

"CO digestion," as defined herein, refers to the exposure of a sample comprising zero-valent transition metal with CO such that the CO reacts with the zero-valent transition metal to form metal carbonyl species that can be extracted from the sample material.

"Quantitative evaluation," as defined herein, generally refers to the determination of species quantity and/or concentration with a high level of precision. In contrast, "qualitative evaluation" generally describes a lower level of precision, but still at a level capable of being used for predictive determinations.

An "assay," according to the present invention, generally refers to a quantitative or qualitative analysis (i.e., evaluation) of a sample. To assay a sample is to subject it to quantitative or qualitative analysis.

In some embodiments, the present invention is directed to a process comprising: exposing a sample that potentially comprises ZVTM to carbon monoxide in an exposure environment such that the carbon monoxide reacts with at least some of the ZVTM, if present, to form metal carbonyl species within the exposure environment subsequent to carbon monoxide exposure; and analyzing the exposure environment, subsequent to sample exposure, for metal carbonyl species, wherein such analyzing for metal carbonyl species yields information about the levels of ZVTM potentially present in said sample. Such a process of reacting CO is termed "digestion" herein, wherein CO digestion of metallic particles of ZVTM from a solid state into a gaseous state as metal carbonyls in the case of Ni & Fe or into solution in the case of Co.

In some or other embodiments, the sample is sedimentary rock. In such embodiments, the present invention is directed to a process comprising: providing sedimentary rock sample potentially comprising a quantity of at least one zero-valent transition metal; exposing the sedimentary rock sample to carbon monoxide in an exposure environment under conditions effective for reacting (i.e., digesting) at least some of the zero-valent transition metal potentially present with carbon monoxide to form metal carbonyl species; and analyzing the exposure environment, after a time sufficient to allow for at least some of the potentially-present ZVTM to react with the carbon monoxide, so as to establish the presence (or absence) of such species within the sample.

Figure 1:
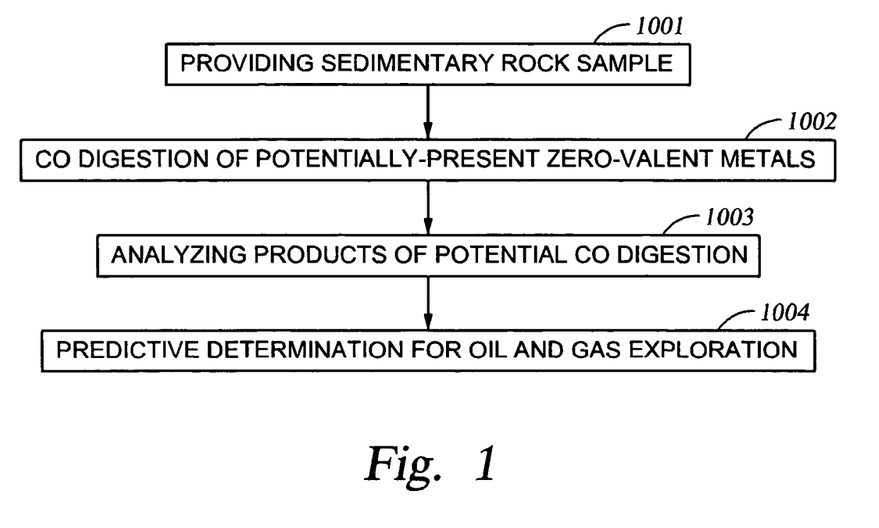
FIG. 1 depicts one or more embodiments of the present invention, in flow diagram form, wherein sedimentary rocks are assayed for ZVTM for the purpose of making predictive determinations for oil and gas exploration.

In some of the above-described embodiments, the quantification of the metal carbonyl and corresponding zero-valent transition metal presence in and/or on the sedimentary rocks is used in making predictive determinations relevant to oil/gas exploration. Such predictive determinations are based upon the required presence of ZVTM for catalytic conversion of heavier hydrocarbons to natural gas (Mango, "The origin of light hydrocarbon," *Geochimica et Cosmochimica Acta*, 64:1265-1277, 2000). For example, outer-neritic shales (black shales) are one of the richest sources of transition metals in sedimentary rocks, and reservoirs comprising such shales are much more likely to be active reservoirs, i.e., gas habitats as opposed to oil habitats. Referring to FIG. 1, such processes (assays) generally comprise the following steps: providing sedimentary rock sample potentially comprising a quantity of at least one zero-valent transition metal (Step 1001); exposing the sedimentary rock sample to carbon monoxide in an exposure environment under conditions effective for reacting (i.e., digesting) at least some of the zero-valent transition metal potentially present with carbon monoxide to form metal carbonyl species (Step 1002); analyzing the exposure environment after a time sufficient to allow for at least some of the potentially-present ZVTM to react with the carbon monoxide so as to establish the presence of such species within the sample (Step 1003); and using the results of Step 1003 to make predictive determinations related to oil and gas exploration (Step 1004) by projecting assay values from a drilled reservoir A to a target reservoir B of similar composition (basis regional geology) under consideration for drilling. Given similar concentrations of ZVTM in A and B, the temperature of B, and the residence time at that temperature, the critical concentration of ZVTM separating oil and gas habitats can be calculated thus giving the habitat of target reservoir B. If reservoir B is sufficiently removed from natural gas markets, then the economic incentives for drilling an oil habitat greatly outweigh those for drilling a gas habitat.

In some embodiments, zero-valent transition metal reaction with carbon monoxide (CO digestion) is primarily a surface phenomenon. In such cases, the levels of ZVTM, relative to the surface area and/or surface area per unit mass of the sample, can be quantified. An exemplary method of determining surface area is by BET analysis. BET stands for Brunauer, Emmet, and Teller, the three scientists who optimized the theory of measuring surface area via the physisorption of gas.

In some cases, it may be desirable to maintain samples in an inert atmosphere/environment prior to CO exposure and/or subsequent analysis of the exposure environment. Suitable inert atmospheres include, but are not limited to, Ar, He, $N_2$, Kr, and combinations thereof.

Depending on the embodiment and sample, one or more ZVTM may be digested and analyzed for the corresponding transition metal carbonyl. As noted above, the presence of ZVTM in samples is probed indirectly by first digesting them with carbon monoxide (CO). This digestion process is described generally in Equation 1. Depending on their surface concentration and/or on the permeability of the sample, the quantity digested by CO may represent only a small fraction of the zero-valent transition metal(s) in the totality of the sample.

$$M + nCO \rightleftharpoons M(CO)_n \quad \text{(Eq. 1)}$$

Digestion of zero-valent transition metal by exposure to CO, according to the present invention, generally takes place in an exposure environment. In addition to CO, this exposure environment may comprise one or more other species. In some embodiments, the exposure environment comprises inert gases. The exposure environment further comprises environmental conditions such as temperature and pressure. Generally, the temperature of the exposure environment is between about 20° C. and about 200° C., and more specifically between about 50° and about 100° C. In some embodiments, pressure, especially that of CO, can be modulated to enhance the favorability of $M(CO)_n$ formation. Generally, methods for quantifying amounts of ZVTM in samples should account for variation in environmental conditions. Typically, the CO exposure comprises a duration that is between about 10 minutes and about one hour, but such exposure duration can vary widely depending upon ZVTM concentration and digestion parameters.

In some embodiments of the present invention, the sample being assayed undergoes one or more preparative processes prior to being exposed to the CO. Such preparative processes may include, but are not limited to, grinding the rock to small particles to expose more rock surface thus enhancing metal digestion. This can be accomplished with mortar and pestle by hand or mechanically milling by placing the rock samples in a closed brass cylinder containing a brass ball and shaking the cylinder with a mechanical 'paint shaker' for a short period of time, typically 15 minutes. Mechanical rock crushing in brass prevents sample contamination by transition metals in steel cylinders and balls. Because mechanical rock crushing can generate heat and thus promote the oxidation of ZVTM if mechanical crushing is carried out in air, it is best to seal the cylinder in an inert atmosphere free of oxygen.

In some embodiments, the above-described preparative processes may comprise one or more contamination control measures, wherein such contamination control measures are employed when handling samples prior to or during the analytical processes of the present invention. In some embodiments, "side wall" rock samples are assayed.

The ZVTM analyzable by methods and processes of the present invention include all ZVTM that suitably react to form metal carbonyl species in accordance with the methods and processes of the present invention. For the purposes of oil and gas exploration, these include, but are not limited to, iron (Fe), cobalt (Co), and nickel (Ni). Such ZVTM, when exposed to CO in a suitable exposure environment, react with the CO to yield digestion products $Fe(CO)_5$, $(Co(CO)_4)_2$, and $Ni(CO)_4$, respectively. In general, such digestion products have the formula: $M(CO)_n$, where M is a transition metal. As previously mentioned, transition metals with non-zero oxidation states do not react with CO under digestion conditions to form metal carbonyl species and are therefore not digested. It is essential to insure that metal oxide reduction by CO does not occur under the conditions of digestion (temperature, CO pressure, and time). In the case of NiO, for example, this reaction can lead inadvertently to $Ni(CO)_4$: $NiO + 5 CO \rightarrow CO_2 + Ni(CO)_4$.

Analysis of the one or more transition metal carbonyl species can be carried out with a variety of existing analytical and/or separation techniques. In some embodiments, the metal carbonyl species, if present, are detected by a chromatographic method such as, but not limited to, gas chromatography. Suitable gas chromatographic (GC) methods include, but are not limited to, gas chromatography-mass spectrometry (GC-MS), gas chromataography-electron capture detection (GC-ECD), gas chromatography-pulsed flame photometric detection (GC-PFPC), gas chromatography-Fourier transform infrared spectroscopy detection (GC-FTIR), and combinations thereof. In some or other embodiments, spectroscopic techniques are employed in quantifying the levels of metal carbonyl species potentially produced, with or without the use of chromatographic separation techniques. In some or other embodiments, mass spectrometric techniques are employed, with or without the use of chromatographic separation techniques, to quantify the levels of metal carbonyl species potentially produced. GC-ECD is an exceptionally well-suited technique for analyzing transition metal carbonyl species in accordance with the processes of the present invention.

In some embodiments, analysis of the one or more transition metal carbonyl species is carried out by means of an integrated process. Such integrated processes may involve, for example, a sample loop by which a volume of the exposure environment can be analyzed by one or more of the above-mentioned analysis techniques post-digestion. In some or other embodiments, a aliquot of the exposure environment is taken (e.g., in an evacuated gas sampling container), then transferred to one or more instruments for analysis by one or more of the above-described analysis methods.

Most generally, the present invention is directed to methods of making predictive determinations of whether a reservoir is active or inactive, in accordance with the oil-to-gas catalytic model, by assaying the surrounding sedimentary rock for ZVTM.

The following Example is provided to demonstrate particular embodiments of the present invention. It should be appreciated by those of skill in the art that the methods disclosed in the Example which follows merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE

This Example serves to illustrate a method by which the present invention can be used to assay sedimentary rock for ZVTM.

CO reacts with zero-valent Ni(Ni$^0$) under mild conditions (~50° C.) to yield nickel tetracarbonyl (Ni(CO)$_4$) (Cotton et al., *Advanced Inorganic Chemistry 6$^{th}$ Edition,* John Wiley & Sons, New York, 1999), a volatile compound boiling at ~40° C. The reaction is specific to Ni$^0$, in that nickel present in higher oxidation states does not react with CO under these conditions.

Figure 2:
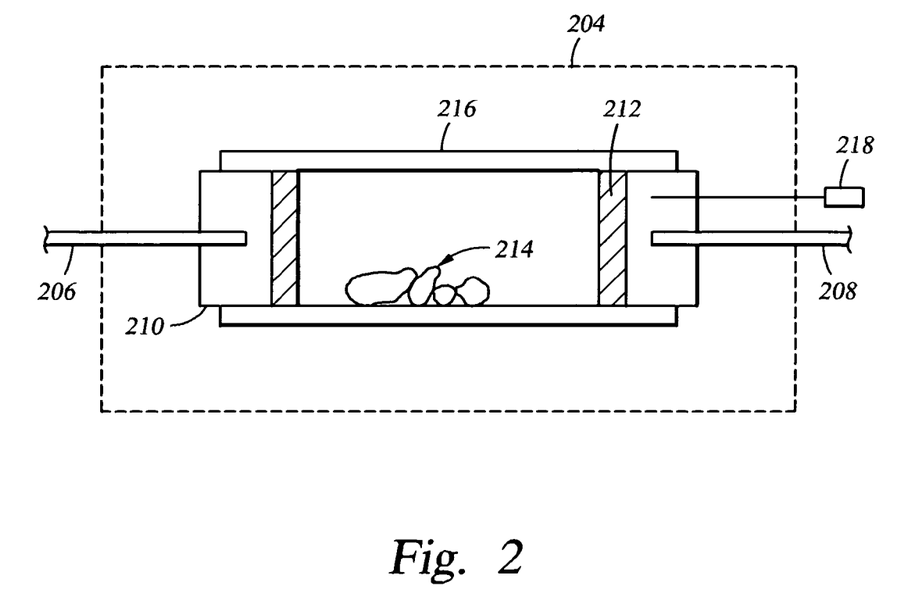
FIG. 2 depicts a reaction vessel for CO digestion of ZVTM in accordance with embodiments of the present invention.
Figure 3:
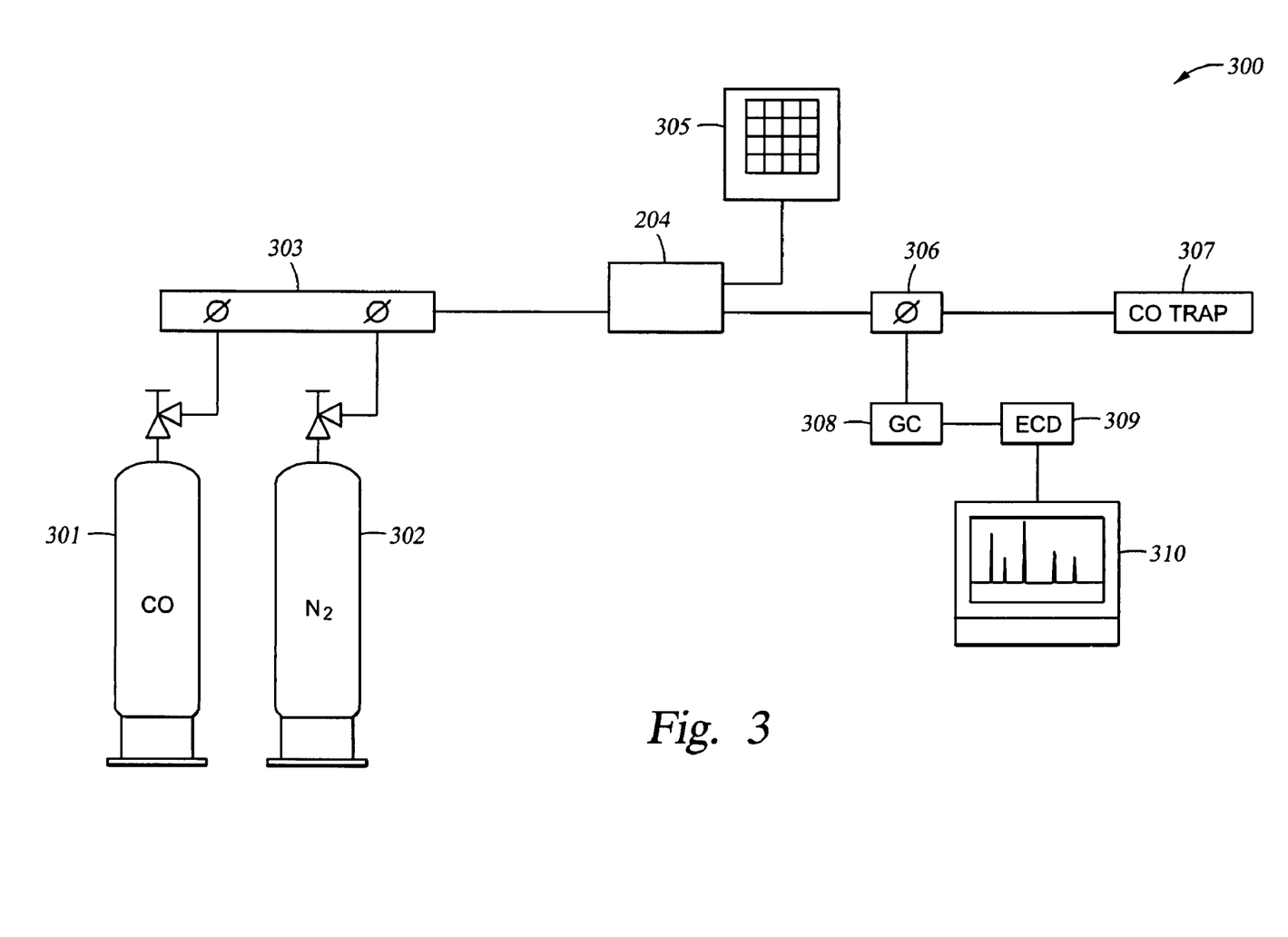
FIG. 3 depicts a reaction system comprising a reaction vessel for CO digestion of ZVTM, as well as a means for analyzing transition metal carbonyl species produced by such CO digestion.

Such reactions are generally carried out in a suitable reaction vessels and gas transfer tubbing that do not contain Ni, Co, or Fe, for example brass, copper, or any of various polymers capable of containing CO under digestion conditions. FIGS. 2 and 3 provid a suitable exposure environment in accordance with the methods and processes of the present invention. Referring to FIG. 2, reaction vessel 204 comprises a reaction tube 210 with a gas inlet 206 and a gas outlet 208. Sample 214 is placed in reaction tube 210 and may be shielded with particulate filters 212. Reaction tube 210 can be heated with heating element 216, wherein reaction temperature can be monitored with a thermocouple device 218. Referring to FIG. 3, reaction vessel 204 is integrated into reaction system 300, wherein reaction system 300 can comprise a CO gas source 301, an inert gas source 302, a gas manifold 303, reaction vessel 204, thermocouple readout 305, switching valve/sampling loop 306, a CO trap 307, and a gas chromatograph 308 coupled to an electron capture detector 309 and controlled by a computer 310. The reaction system should be constructed so as to be operable at required reaction temperatures and to comprise materials that, under analysis conditions, will not interfere in the analysis process.

Figure 4:
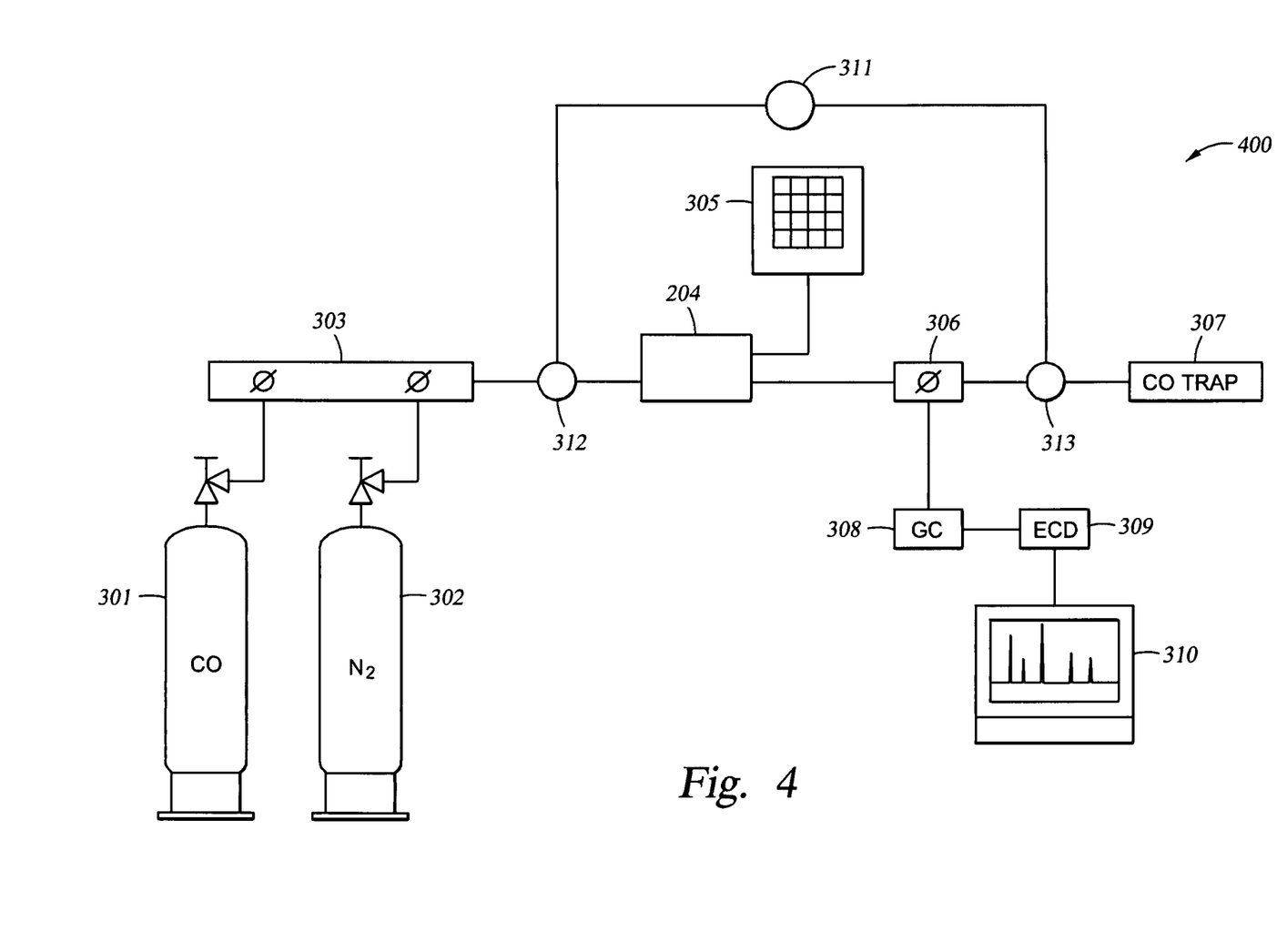
FIG. 4 depicts a variant reaction system comprising two 3-way valves that are inserted into the manifold-to-CO trap line of the reaction system depicted in FIG. 3 creating a closed loop through which digestion gases are circulated using an in-line pump.

In a variation of the above-described reaction system, a variant reaction system 400, shown in FIG. 4, comprises two 3-way valves (312 and 313) that are inserted into the manifold-to-CO trap line as shown creating a closed loop through which digestion gases are circulated using an in-line pump (311). Aliquots of digestion gas are taken through 306 and analyzed through 308 and 309 for nickel and iron carbonyl until their concentrations are constant, thereby signaling digestion completion. Cobalt carbonyl remaining in the digestion chamber 204 can be solvent-extracted from the samples and analyzed directly by injecting an aliquot of the liquid extract into the inlet septum of the GC.

For a typical analysis, a reaction vessel 204 (~10 ml) containing ~1 gm of sedimentary rock is heated in CO to ~50° C. for sufficient time to digest any zero-valent metals dispersed on the rock's surface. An aliquot of gas phase product, taken from the exposure environment (the reaction vessel) via the switching valve/sampling loop 306 and is then analyzed by standard gas chromatography (GC) with electron capture detection (ECD), which detects nickel and iron carbonyls at ~100 ppbv levels. This assay, therefore, is capable of detecting ppb zero-valent metals.

Variations on this procedure should similarly detect zero-valent Co and Fe. Fe(CO)$_5$ boils at 103° C. and thus can be detected along with Ni(CO)$_4$ at higher digestion temperatures. (Co(CO)$_4$)$_2$ boils and/or decomposes at a much higher temperature and thus should remain in the liquid phase, probably dispersed on the rock's surface. Liquid extraction should give a (Co(CO)$_4$)$_2$ solution readily analyzed for (Co(CO)$_4$)$_2$ by GC. In general, the overall procedure is simple, extremely sensitive, and flexible. Higher temperatures and CO pressures could be chosen to accelerate digestion.

Thus, in light of the foregoing, the present invention provides extremely sensitive (parts-per-billion) assays, specific to ZVTM, based on the reaction of carbon monoxide and ZVTM yielding corresponding metal carbonyl species. The extraction of transition metal carbonyls from sedimentary rocks by CO digestion is unequivocal evidence for zero-valent metals dispersed on the rock's surface. Because this assay is specific to ZVTM and catalytic oil-to-gas is specific to ZVTM (Mango, "The origin of light hydrocarbons," *Geochimica et Cosmochimica Acta,* 64:1265-1277, 2000), this assay is specific to catalytic oil-to-gas. Furthermore, such methods represent an improvment over existing methods of zero-valent transition metal detection (e.g., ultra-high vacuum X-ray photoelectron spectroscopy, anodic striping voltammetry, etc.) in that they are quite simple.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A process comprising the steps of:
   a) placing a sample that potentially comprises zero-valent transition metal in an inert environment;
   b) exposing the sample to carbon monoxide in an exposure environment comprising carbon monoxide, such that the carbon monoxide reacts with at least some of the zero-valent transition metal, if present, to form metal carbonyl species within said exposure environment;
      wherein the exposing step is carried out at a temperature and carbon monoxide pressure over a period of time such that any metal oxide present in the sample is not reduced by carbon monoxide; and
   c) analyzing the exposure environment, subsequent to sample exposure, for metal carbonyl species, wherein said analyzing for metal carbonyl species yields information about the levels of zero-valent transition metal present in said sample.

2. The process of claim 1 further comprising a step of determining the surface area per unit mass of the sample.

3. The process of claim 2, wherein the step of determining the surface area per unit mass of the sample comprises BET analysis.

4. The process of claim 1, wherein the sample is maintained in a controlled environment prior to being exposed to carbon monoxide.

5. The process of claim 4, wherein the controlled environment comprises an inert gas selected from the group consisting of Ar, N$_2$, He, Kr, and combinations thereof.

6. The process of claim 1, wherein the step of exposing comprises an exposure temperature between about 20° C. and about 200° C.

7. The process of claim 1, wherein the step of exposing comprises an exposure duration between about 10 minutes and about 1 hour.

8. The process of claim 1 further comprising a step of sample preparation carried out before the step of exposing, wherein said sample preparation comprises a technique selected from the group consisting of grinding, milling, shaking, and combinations thereof.

9. The process of claim 1, wherein the metal carbonyl species potentially formed are selected from the group consisting of $Fe(CO)_5$, $Ni(CO)_4$, $(Co(CO)_4)_2$, and combinations thereof.

10. The process of claim 1, wherein analyzing the exposure environment subsequent to sample exposure is done by chromatography.

11. The process of claim 1, wherein analyzing the exposure environment subsequent to sample exposure is done by a gas chromatographic technique selected from the group consisting of GC-ECD, GC-PFPC, GC-MS, GC-FTIR, and combinations thereof.

12. A rock assay comprising the steps of:
  a) providing sedimentary rock sample potentially comprising a quantity of at least one zero-valent transition metal in an inert environment;
  b) exposing said sedimentary rock sample to carbon monoxide in an exposure environment under conditions effective for reacting at least some of the zero-valent transition metal potentially present with carbon monoxide to form metal carbonyl species;
    wherein the exposing step is carried out at a temperature and carbon monoxide pressure over a period of time such that any metal oxide present in the sample is not reduced by carbon monoxide; and
  c) analyzing the exposure environment, after a time sufficient to allow for at least some of the potentially-present zero-valent transition metal to react with the carbon monoxide, so as to establish the presence of such species within the sample.

13. The rock assay of claim 12 further comprising a step of determining the surface area per unit mass of the sedimentary rock sample.

14. The rock assay of claim 13, wherein the step of determining the surface area per unit mass of the sedimentary rock sample comprises BET analysis.

15. The rock assay of claim 14, wherein the sedimentary rock sample is maintained in a controlled environment prior to being exposed to carbon monoxide.

16. The rock assay of claim 15, wherein the controlled environment comprises an inert gas selected from the group consisting of Ar, $N_2$, He, Kr, and combinations thereof.

17. The rock assay of claim 12, wherein the step of exposing comprises an exposure temperature between about 20° C. and about 200° C.

18. The rock assay of claim 12, wherein the step of exposing comprises an exposure duration between about 10 minutes and about 1 hour.

19. The rock assay of claim 12 further comprising a step of sample preparation done before the step of exposing, wherein said sample preparation comprises a technique selected from the group consisting of grinding, milling, shaking, and combinations thereof.

20. The rock assay of claim 12, wherein the metal carbonyl species potentially formed are selected from the group consisting of $Fe(CO)_5$, $Ni(CO)_4$, $(Co(CO)_4)_2$, and combinations thereof.

21. The rock assay of claim 12, wherein analyzing the exposure environment subsequent to sample exposure is done by chromatography.

22. The rock assay of claim 12, wherein the step of analyzing the exposure environment, after a time sufficient to allow for at least some of the potentially-present zero-valent transition metals to react with the carbon monoxide, is done by a gas chromatographic technique selected from the group consisting of GC-ECD, GC-PFPC, GC-MS, GC-FTIR, and combinations thereof.

23. A rock assay comprising the steps of:
  a) providing sedimentary rock sample potentially comprising a quantity of at least one zero-valent transition metal in an inert atmosphere;
  b) exposing said sedimentary rock sample to carbon monoxide in an exposure environment under conditions effective for reacting at least some of the zero-valent transition metal potentially present with carbon monoxide to form metal carbonyl species;
    wherein the exposing step is carried out at a temperature and carbon monoxide pressure over a period of time such that any metal oxide present in the sample is not reduced by carbon monoxide;
  b) analyzing the exposure environment, after a time sufficient to allow for any potentially-present zero-valent transition metal to react with the carbon monoxide so as to establish the presence of such species within the sample by way of analysis results; and
  c) comparing analysis results to established values correlatable with known geologic reservoir content for the purpose of making predictive determinations related to oil and gas exploration.

24. The rock assay of claim 23 further comprising a step of determining the surface area per unit mass of the sedimentary rock sample.

25. The rock assay of claim 24, wherein the step of determining the surface area per unit mass of the sedimentary rock sample comprises BET analysis.

26. The rock assay of claim 23, wherein the sedimentary rock sample is maintained in a controlled environment prior to being exposed to carbon monoxide.

27. The rock assay of claim 26, wherein the controlled environment comprises an inert gas selected from the group consisting of Ar, $N_2$, He, Kr, and combinations thereof.

28. The rock assay of claim 23, wherein the step of exposing comprises an exposure temperature between about 20° C. and about 200° C.

29. The rock assay of claim 23, wherein the step of exposing comprises an exposure duration between about 10 minutes and about 1 hour.

30. The rock assay of claim 23 further comprising a step of sample preparation carried out before the step of exposing, wherein said sample preparation comprises a technique selected from the group consisting of grinding, milling, shaking, and combinations thereof.

31. The rock assay of claim 30, wherein contamination control measures are utilized during the sample preparation step.

32. The rock assay of claim 23, wherein the metal carbonyl is selected from the group consisting of $Fe(CO)_5$, $Ni(CO)_4$, $(Co(CO)_4)_2$, and combinations thereof.

33. The rock assay of claim 23, wherein analyzing the exposure environment subsequent to sample exposure is done by gas chromatography.

34. The rock assay of claim 23, wherein the step of analyzing the exposure environment, after a time sufficient to allow for at least some of the potentially-present zero-valent transition metals to react with the carbon monoxide, is done by a gas chromatographic technique selected from the group consisting of GC-ECD, GC-PFPC, GC-MS, GC-FTIR, and combinations thereof.

* * * * *